United States Patent [19]

Ozaki et al.

[11] Patent Number: 5,284,860
[45] Date of Patent: Feb. 8, 1994

[54] TRIAZOLE DERIVATIVES AND INSECTICIDES

[75] Inventors: Masami Ozaki; Reijiro Honami; Takashi Yumita; Atsuhiko Ikeda, all of Iwata; Naokazu Minoguchi; Norihiko Izawa, both of Ogasa; Tadayoshi Hirano, Kakegawa, all of Japan

[73] Assignees: Kumiai Chemical Industry Co. Ltd.; Ihara Chemical Industry Co., Ltd., Tokyo, Japan

[21] Appl. No.: 956,980

[22] Filed: Oct. 6, 1992

[30] Foreign Application Priority Data

Mar. 4, 1992 [JP] Japan .................... 4-081412

[51] Int. Cl.$^5$ .................... C07D 401/04; A61K 31/44
[52] U.S. Cl. .................... 514/340; 546/276
[58] Field of Search .................... 546/276; 514/340

[56] References Cited

U.S. PATENT DOCUMENTS

| | | | |
|---|---|---|---|
| 4,011,218 | 3/1977 | Baldwin et al. | 546/276 |
| 4,414,221 | 11/1983 | Parsons et al. | 514/383 |
| 4,788,210 | 11/1988 | Lüthy et al. | 514/383 |

FOREIGN PATENT DOCUMENTS

| | | |
|---|---|---|
| 185256 | 6/1986 | European Pat. Off. . |
| 0217552 | 4/1987 | European Pat. Off. . |
| 3631511 | 9/1986 | Fed. Rep. of Germany . |

OTHER PUBLICATIONS

Research Disclosure, vol. 278, Jun. 1987, pp. 356-357.

Primary Examiner—Jane T. Fan
Attorney, Agent, or Firm—Stevens, Davis, Miller & Mosher

[57] ABSTRACT

A novel triazole derivative for use in an insecticide has a general formula [I]:

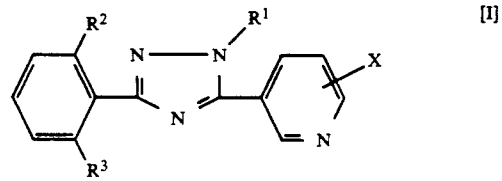

(wherein $R^1$ is a lower alkyl group, $R^2$ and $R^3$ are same or different halogen atoms and X is a chlorine atom located at 2- or 6-position) and controls various injurious insects, particularly aphids without damaging crops.

4 Claims, No Drawings

TRIAZOLE DERIVATIVES AND INSECTICIDES

BACKGROUND OF THE INVENTION

1. Field of the Invention

This invention relates to a novel triazole derivative useful as an insecticide as well as an insecticide containing the same as an active ingredient.

2. Description of the Related Art

It is known that triazole derivatives such as 3-chlorophenyl -5-chloropyridyl-1-methyl-1H-1,2,4-triazole and the like are effective for the control of mites and sap-sucking insects (Research Disclosure RD278004). In this literature, however, there is no description that what concentration of the above derivative is effective to what kind of injurious insect and also the origin for these derivative is unclear. Further, the compounds concretely described in the above literature are poor in the systemic translocation and the systemic penetrance and are hardly said to be satisfactory as an insecticide.

As an injurious insect harming farm and garden products, there are aphides such as cotton aphid, green peach aphid, foxglove aphid and the like. These aphides eat growing points of plants to badly damage farm and garden products and also they infect virus. Therefore, it is strongly demanded to control these aphides. Lately, injurious insects developing resistance to existing insecticide and acaricide appear and the control thereof becomes more serious. In this connection, chemicals for controlling hemiptera insects typified by aphides are desirable to have systemic translocation and systemic penetrance as a functional performance.

SUMMARY OF THE INVENTION

The inventors have synthesized various triazole derivatives in order to develop an insecticide useful for the control of the above injurious insects and made studies with respect to their physiological activities. As a result, the inventors have found that novel compounds having a general formula [I] as mentioned later have excellent systemic translocation and systemic penetrance and develop excellent insecticidal activity to various injurious insects and acarids as compared with the compounds concretely described in the aforementioned literature, and the invention has been accomplished.

According to the invention, there is the provision of a triazole derivative having the following general formula [I]:

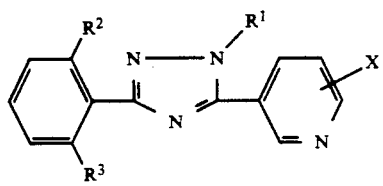

(wherein $R^1$ is a lower alkyl group, $R^2$ and $R^3$ are same or different halogen atoms and X is a chlorine atom located at 2- or 6-position).

DESCRIPTION OF THE PREFERRED EMBODIMENTS

In the triazole derivatives according to the invention, the systemic translocation activity and the systemic penetrance activity are particularly improved because both $R^2$ and $R^3$ as a substituent on benzene ring bonded to 3-position of triazole ring are halogen atoms. Furthermore, the triazole derivatives having disubstituents on benzene ring bonded to 3-position of triazole ring and an alkyl substituent on 1-position of triazole ring are possible to be synthesized by novel production methods.

In the general formula [I], the lower alkyl group as $R^1$ includes methyl group, ethyl group, propyl group, isopropyl group, butyl group, isobutyl group, t-butyl group, s-butyl group and the like, while the halogen atom as $R^2$ and $R^3$ includes fluorine, chlorine, bromine and iodine. Among the compounds of the general formula [I], a compound in which $R^1$ is methyl or ethyl group and X is a chlorine atom located at 2- or 6-position is preferable.

The compounds of the general formula [I] according to the invention are shown in Table 1. And also, the compound No. is referred in subsequent description.

TABLE 1

| Compound No. | $R^1$ | $R^2$ | $R^3$ | X | Physical properties melting point (°C.) or refractive index ($n_D^{20}$) |
|---|---|---|---|---|---|
| 1 | CH$_3$ | F | F | 2-Cl | 167.0~171.0 |
| 2 | CH$_3$ | F | Cl | 2-Cl | 48.0~52.0 |
| 3 | CH$_3$ | Cl | Cl | 2-Cl | 133.0~135.5 |
| 4 | C$_2$H$_5$ | F | Cl | 2-Cl | 101.0~103.0 |
| 5 | C$_3$H$_7$-i | F | Cl | 2-Cl | 156.0~160.0 |
| 6 | CH$_3$ | F | F | 6-Cl | 138.0~141.0 |
| 7 | CH$_3$ | F | Cl | 6-Cl | 118.5~120.5 |
| 8 | CH$_3$ | Cl | Cl | 6-Cl | 167.0~171.0 |
| 9 | CH$_3$ | F | I | 6-Cl | 40.0~42.0 |
| 10 | C$_2$H$_5$ | F | Cl | 6-Cl | 102.0~105.0 |
| 11 | C$_3$H$_7$-i | F | Cl | 6-Cl | not measurable |

The compounds according to the invention can be produced according to the following methods, but it is not intended to restrict these methods.

Production Method 1-1

The compound of the general formula [I] can be obtained by reacting an alkyl N-acylimidate derivative or alkyl N-acylthioimidate ester derivative represented by a general formula [II] with a hydrazine derivative represented by a general formula [III] in an inert solvent according to the following reaction formula:

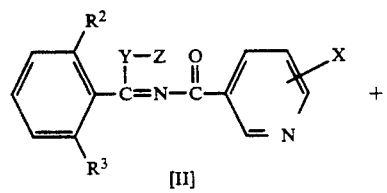

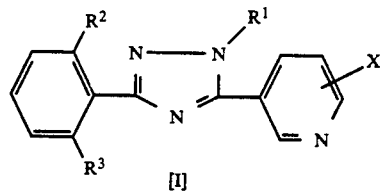

(wherein Y is a sulfur atom or an oxygen atom, Z is a lower alkyl group, and $R^1$, $R^2$, $R^3$ and X are the same as described above).

As the inert solvent, use may be made of any solvents not obstructing the reaction, which includes an alcohol such as methanol, ethanol or the like; an ether such as diethyl ether, tetrahydrofuran, dioxane, diglyme or the like; an aliphatic hydrocarbon such as pentane, hexane, petroleum ether or the like; a halogenated hydrocarbon such as dichloromethane, dichloroethane, chloroform, carbon tetrachloride or the like; a nitrile such as acetonitrile or the like; N,N-dimethylformamide, N,N-dimethylacetamide, dimethylsulfoxide, water and a mixture thereof. Moreover, the hydrazine derivative [III] is usually used in an amount of 1–5 moles per 1 mole of the alkyl N-acylimidate derivative or alkyl N-acylthioimidate ester derivative [II].

The reaction temperature is optional within a range of from 0° C. to a boiling point of the solvent used, but is preferably within a range of 0° C. to 50° C. The reaction time is dependent upon the starting compounds used, but is usually within a range of 1–72 hours.

A concrete example of this reaction is disclosed, for instance, in Synthesis, 483 (1983).

The alkyl N-acyl(thio) imidate derivative [II] as a starting compound can be produced by the following method.

Production Method 1-2

The alkyl N-acyl(thio) imidate derivative represented by the general formula [II] can be obtained by reacting benzimidate derivative represented by a general formula [IV] with a nicotinoylhalide derivative represented by a general formula [V] in an inert solvent in the presence of a base according to the following reaction formula:

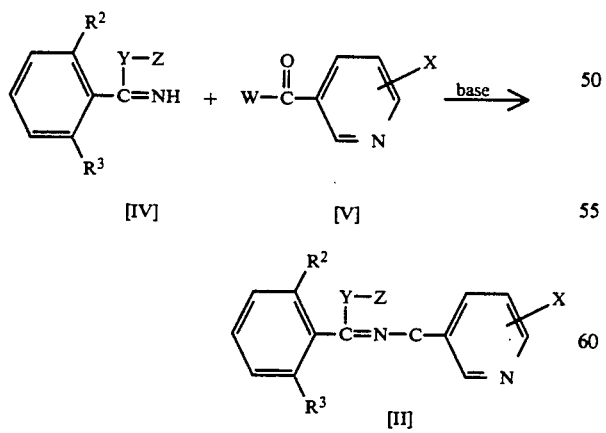

(wherein W is a halogen atom, and $R^2$, $R^3$, X, Y and Z are the same as mentioned above).

Moreover, the benzimidate derivative of the general formula [IV] may be used as an acid addition salt. In this case, boron tetrafluoride, hydrogen chloride, hydrogen bromide, hydrogen iodide or the like may be used.

As the base, use may be made of inorganic bases such as sodium carbonate, potassium carbonate, sodium hydrogen carbonate, sodium hydroxide, potassium hydroxide and the like; or organic bases such as diethylamine, triethylamine, pyridine, 4-N,N-dimethylamino pyridine and the like. As the solvent, mention may be made of a ketone such as acetone, methyl ethyl ketone or the like; an ether such as diethyl ether, tetrahydrofuran, dioxane, diglyme or the like; an aromatic hydrocarbon such as benzene, toluene, chlorobenzene or the like; an aliphatic hydrocarbon such as pentane, hexane, petroleum ether or the like; a halogenated hydrocarbon such as dichloromethane, dichloroethane, chloroform, carbon tetrachloride or the like; a nitrile such as acetnitrile or the like; dimethylformamide, dimethylacetamide, dimethylsulfoxide and a mixture thereof.

In general, the nicotinoylhalide derivative [V] is used in an amount of 0.8–1.3 moles per 1 mole of the benzimidate derivative [IV]. The amount of the base used is 1.0–2.0 mol equivalent per 1 mole of the benzimidate derivative [IV].

The reaction time is dependent upon the starting compounds used, but is usually within a range of 1–24 hours. The reaction temperature is within a range of from 0° C. to a boiling point of the solvent used.

Production Method 2

The compound of the general formula [I] according to the invention can be obtained by reacting an N-(phenylsulfonyl) benzhydrazonoyl chloride derivative represented by a general formula [VI] with 3-cyanopyridine derivative represented by a general formula [VII] in an inert solvent in the presence of Lewis acid according to the following reaction formula:

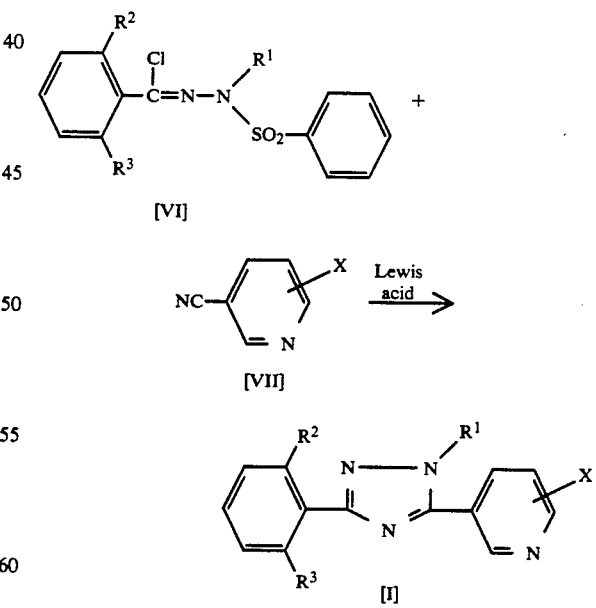

(wherein $R^1$, $R^2$, $R^3$ and X are the same as mentioned above).

As the inert solvent, use may be made of any solvents not obstructing the reaction, which includes an ether such as diethyl ether, tetrahydrofuran, dioxane, diglyme or the like; an aromatic hydrocarbon such as benzene, toluene, chlorobenzene, dichlorobenzene or the like; an aliphatic hydrocarbon such as pentane, hexane, petroleum ether or the like; a halogenated hydrocarbon such as dichloromethane, dichloroethane, chloroform, carbon tetrachloride or the like; dimethylformamide, dimethylacetamide, dimethylsulfoxide or a mixture thereof. In general, 3-cyanopyridine derivative [VII] and Lewis acid are used in an amount of 1.0–2.0 moles per 1 mole of N-(phenylsulfonyl) benzhydrazonoyl chloride derivative [VI], respectively.

The reaction temperature is optional within a range of from 0° C. to a boiling point of the solvent used, but is preferably within a range of 50° C. to 150° C. The reaction time is dependent upon the starting compounds used, but is usually within a range of 30 minutes to 5 hours.

A concrete example of this reaction is disclosed, for instance, in BULLETIN of the CHEMICAL SOCIETY of JAPAN, vol. 56, pages 545–548 (1983).

Production Method 3

The compound of the general formula [I] according to the invention can be obtained by reacting an N-(phenylsulfonyl) benzamidrazone derivative represented by a general formula [VIII] with the nicotinoylhalide derivative of the general formula [V] in an inert solvent according to the following reaction formula:

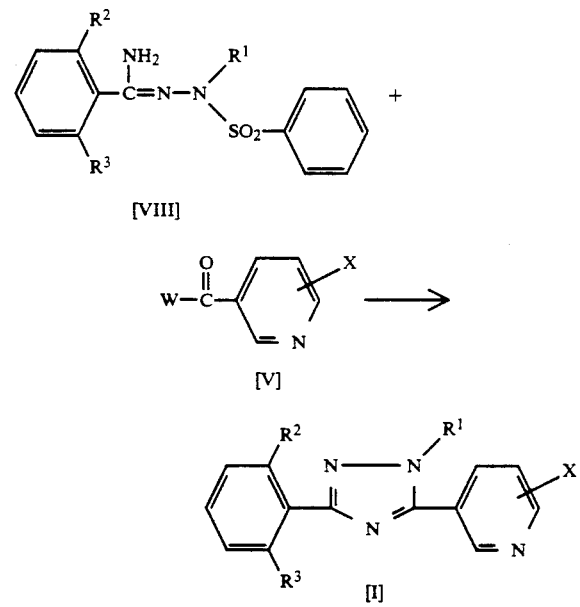

(wherein $R^1$, $R^2$, $R^3$, W and X are the same as mentioned above).

As the inert solvent, use may be made of any solvents not obstructing the reaction, which includes an ether such as diethyl ether, tetrahydrofuran, dioxane, diglyme or the like; an aromatic hydrocarbon such as benzene, toluene, chlorobenzene or the like; an aliphatic hydrocarbon such as pentane, hexane, petroleum ether or the like; a halogenated hydrocarbon such as dichloromethane, dichloroethane, chloroform, carbon tetrachloride or the like; dimethylformamide, dimethylacetamide, dimethylsulfoxide or a mixture thereof. In general, the nicotinoylhalide derivative [V] is used in an amount of 1.0–2.0 mole per 1 mole of N-(phenylsulfonyl) benzamidrazone derivative [VIII].

The reaction temperature is optional within a range of from 0° C. to a boiling point of the solvent used, but is preferably within a range of 50° C. to 200° C. The reaction time is dependent upon the starting compounds used, but is usually within a range of 30 minutes to 5 hours.

A concrete example of this reaction is disclosed, for instance, in BULLETIN of the CHEMICAL SOCIETY of JAPAN, vol. 56, pages 545–548 (1983).

Moreover, the N-(phenylsulfonyl) benzamidrazone derivative [VIII] as a starting compound can be produced by the following method.

Production Method 3-2

The N-(phenylsulfonyl) benzamidrazone derivative represented by the general formula [VIII] can be obtained by reacting the N-(phenylsulfonyl) benzhydrazonoyl chloride derivative of the general formula [VI] with ammonia gas in an inert solvent according to the following reaction formula:

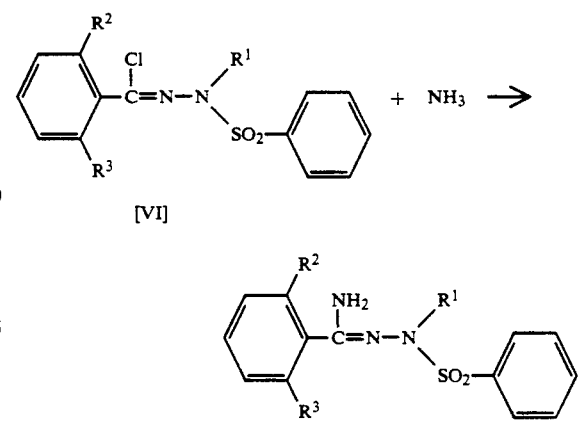

(wherein $R^1$, $R^2$ and $R^3$ are the same as mentioned above).

As the inert solvent, use may be made of any solvents not obstructing the reaction, which includes an ether such as diethyl ether, tetrahydrofuran, dioxane, diglyme or the like; an aromatic hydrocarbon such as benzene, toluene, chlorobenzene or the like; an aliphatic hydrocarbon such as pentane, hexane, petroleum ether or the like; a halogenated hydrocarbon such as dichloromethane, dichloroethane, chloroform, carbon tetrachloride or the like; dimethylformamide, dimethylacetamide, dimethylsulfoxide or a mixture thereof. In general, the ammonia gas is used in an amount of 5.0–10.0 mole per 1 mole of N-(phenylsulfonyl) benzhydrazonoyl chloride derivative [VI].

The reaction temperature is optional within a range of from 0° C. to a boiling point of the solvent used, but is preferably within a range of 50° C. to 150° C. The reaction time is dependent upon the starting compounds used, but is usually within a range of 5 to 20 hours.

A concrete example of this reaction is disclosed, for instance, in BULLETIN of the CHEMICAL SOCIETY of JAPAN, vol. 56, page 547 (1983).

The following examples are given in illustration of the invention and are not intended as limitations thereof.

PRODUCTION EXAMPLE 1

5-(2-chloropyridin-3-yl)-3-(2,6-difluorophenyl)-1-methyl-1H-1, 2,4-triazole (compound 1)

In 100 ml of toluene were dissolved 1.9 g of ethyl-2,6-difluoro benzimidate and 1.2 g of triethylamine, to which was added dropwise 1.8 g of 2-chloronicotinoyl chloride within a temperature range of 5°–10° C. with stirring. The resulting solution was stirred at room temperature for 6 hours. After the completion of the reaction, the reaction solution was washed with an aqueous salt solution and further with water and then the resulting toluene layer was dried over sodium sulfate.

To the toluene layer was added 0.5 g of monomethyl hydrazine, which was reacted at room temperature for 8 hours. After the completion of the reaction, the reaction solution was washed with a diluted hydrochloric acid solution and further with water and then the toluene layer was dried over anhydrous magnesium sulfate and concentrated under a reduced pressure. The resulting concentrate was subjected to a chromatography of silica gel (trade mark: Wakogel C-200) using a mixed solution of hexane and ethyl acetate as a developing solvent to obtain 0.8 g (yield: 25.8%) of a desired yellow granular crystal (melting point: 167.0°–171.0° C.).

NMR data (60 MHz, CDCl$_3$ solvent, δ value);
3.95:(s, 3H),
6,80–7.68:(m, 4H),
7.95:(dd, 1H),
8.55:(dd, 1H).

PRODUCTION EXAMPLE 2

3-(2,6-dichlorophenyl)-5-(2-chloropyridin-3-yl)-1-methyl-1H-1,2,4-triazole (compound 3)

In 50 ml of dichlorobenzene were dissolved 5.7 g of N-methyl-N-phenylsulfonyl-2,6-dichlorobenzohydrazonoyl chloride and 2.3 g of 2-chloro-3-cyanopyridine, to which was added 2.2 g of anhydrous aluminum chloride at room temperature with stirring. The resulting solution was raised to 120°–140° C. in an oil bath and stirred for 4 hours. After the completion of the reaction, the reaction solution was washed with a diluted alkali solution and further with a diluted hydrochloric acid solution. After the washing with water, the organic layer was dried over anhydrous magnesium sulfate and concentrated under a reduced pressure. The resulting concentrate was subjected to a chromatography of silica gel (trade mark: Wakogel C-200) using a mixed solution of hexane and ethyl acetate as a developing solvent to obtain 1.9 g (yield: 37.3%) of a desired light brown granular crystal (melting point: 133.0°–135.5° C.).

NMR data (60 MHz, CDCl$_3$ solvent, δ value);
3.93:(s, 3H),
7.30–7.63 :(m, 4H),
7.95:(dd, 1H),
8.55:(dd, 1H).

PRODUCTION EXAMPLE 3

3-(2-chloro-6-fluorophenyl)-5-(6-chloropyridin-3-yl)-1-methyl-1H-1,2,4-triazole (compound 7)

In 50 ml of 1-methyl-2-pyrrolidone (NMP) were dissolved 8.8 g of N-methyl-N-phenylsulfonyl-2-chloro-6-fluorobenzamidrazone and 4.5 g of 6-chloronicotynoyl chloride. The resulting solution was raised to 110°–120° C. in an oil bath and stirred for 2 hours. It was further raised to 170°–180° C. and stirred for 4 hours. After the completion of the reaction, it was added with 200 ml of chloroform and washed with water. The resulting organic layer was dried over anhydrous magnesium sulfate and concentrated under a reduced pressure. The resulting concentrate was subjected to a chromatography of silica gel (trade mark: Wakogel C-200) using a mixed solution of hexane and ethyl acetate as a developing solvent to obtain 2.0 g (yield: 35.5%) of a desired yellow granular crystal (melting point: 118.5°–120.5° C.).

NMR data (60 MHz, CDCl$_3$ solvent, δ value);
4.03 :(s, 3H),
6.83–7.50:(m, 4H),
8.05:(dd, 1H),
8.75:(dd, 1H).

PRODUCTION EXAMPLE 4

3-(2-chloro-6-fluorophenyl)-5-(6-chloropyridin-3-yl)-1-isopropyl-1H-1,2,4-triazole (compound 11)

In 20 ml of dichlorobenzene were dissolved 5.8 g of N-methyl-N-phenylsulfonyl-2-chloro-6-fluorobenzohydrazonoyl chloride and 2.3 g of 6-chloro-3-cyanopyridine, to which was added 2.2 g of anhydrous aluminum chloride at room temperature with stirring. The resulting solution was raised to 140° C. in an oil bath and stirred for 30 minutes. After the completion of the reaction, the reaction solution was dissolved with 200 ml of chloroform. The chloroform solution was washed with a diluted alkali solution and further with a diluted hydrochloric acid solution. After the washing with water, the organic layer was dried over anhydrous magnesium sulfate and concentrated under a reduced pressure. The resulting concentrate was subjected to chromatography of silica gel (trade mark: Wakogel C-200) using a mixed solution of hexane and ethyl acetate as a developing solvent to obtain 1.0 g (yield: 18.9%) of a desired brown viscous liquid (refractive index ($n_D20$): measurement impossible).

NMR data (60 MHz, CDCl$_3$ solvent, δ value);
1.60 :(d, 6H),
4.45–4.95:(m, 1H),
6.95–7.55:(m, 4H),
7.95:(dd, 1H),
8.65:(d, 1H).

The insecticide according to the invention contains a triazole derivative represented by the general formula [I] as an active ingredient.

When the triazole compounds according to the invention are used as an active ingredient for insecticides, these compounds themselves may be used alone, or may be compounded with a carrier, a surfactant, a dispersing agent, an adjuvant or the like to form dusts, wettable powder, emulsion, fine powder, granulates or the like. As the carrier used in the formulation of agricultural chemicals, mention may be made of a solid carrier such as zeeklite, talc, bentonite, clay, kaolin, diatomaceous earth, white carbon, vermiculite, calcium hydroxide, quartz sand, ammonium sulfate, urea or the like; and a liquid carrier such as isopropyl alcohol, xylene, cyclohexanone, methylnaphthalene or the like. As the surfactant and dispersing agent, mention may be made of a metal salt of alkylbenzene sulfonic acid, a metal salt of dinaphtylmethane disulfonic acid, a sulfuric acid ester of alcohol, alkylarylsulfonate, lignin sulfonate, polyoxyethylene glycol ether, polyoxyethylene alkylaryl ether, polyoxyethylene sorbitan monoalkylate and the like. As the adjuvant, mention may be made of carboxymethylcellulose, polyethylene glycol, gum arabi and the like.

In the formulation, the amount of the active ingredient used may be selected in accordance with the use purpose, but it is properly selected within a range of 0.05-20% by weight, preferably 0.1-10% by weight in case of the dusts and granules. In case of the emulsion and wettable powder, the amount of the active ingredient is properly selected within a range of 0.5-80% by weight, preferably 1-60% by weight.

The insecticide according to the invention may be used by spraying onto stem and leaves, by applying to soil, by applying to a nursery box, by spraying onto water surface or the like. In use, the insecticide is directly applied or sprayed by diluting to a proper concentration. The amount of the insecticide applied is dependent upon the kind of the compound used as an active ingredient, injurious insect to be controlled, tendency and degree of insect injury, environmental condition, kind of formulation used and the like. When the insecticide according to the invention is directly used as dusts or granules, the amount of the active ingredient is properly selected within a range of 0.05 g-5 kg, preferably 0.1-1 kg per 10 are. Furthermore, when it is used in form of a liquid as emulsion or wettable powder, the amount of the active ingredient is properly selected within a range of 0.1-5000 ppm, preferably 1-1000 ppm.

Moreover, the insecticide according to the invention may be used by mixing with other insecticide, fungicide, fertilizer, plant growth regulator and the like.

The formulation will concretely be described with respect to typical examples. In this case, the kind of the compounds and additives and the compounding ratio are not limited to these examples and may be varied within wide ranges. Moreover, % is by weight otherwise specified.

FORMULATION EXAMPLE 1

Emulsion

An emulsion was prepared by uniformly dissolving 30% of the compound 6, 20% of cyclohexanone, 11% of polyoxyethylene alkylaryl ether, 4% of calcium alkylbenzene sulfonate and 35% of methylnaphthaline.

FORMULATION EXAMPLE 2

Wettable powder

A wettable powder was prepared by uniformly mixing and pulverizing 40% of the compound 3, 15% of diatomaceous earth, 15% of clay, 25% of white carbon, 2% of sodium dinaphthylmethane disulfonate and 3% of sodium lignin sulfonate. FORMULATION EXAMPLE 3

Dust

A dust was prepared by uniformly mixing and pulverizing 2% of the compound 1, 5% of diatomaceous earth and 93% of clay.

FORMULATION EXAMPLE 4

Granule

5% of the compound 7, 2% of sodium salt of lauryl alcohol sulfuric acid ester, 5% of sodium lignin sulfonate, 2% of carboxymethyl cellulose and 86% of clay were uniformly mixed and pulverized. Then, 100 parts by weight of the resulting mixture was added with 20 parts by weight of water and kneaded and shaped into granules of 14-32 mesh through an extrusion type granulating machine and dried to form granules.

The triazole derivatives according to the invention are effective to control aphids such as cotton aphid, green peach aphid, cabbage aphid and the like; planthoppers such as brown planthopper, white-backed planthopper, small brown planthopper and the like; leafhoppers such as green rice leafhopper, tea green leafhopper and the like; whiteflies such as greenhouse whitefly and the like; hemipteran injurious insects such as mulberry scale, corbett rice bug and the like; lepidopteran injurious insects such as diamond-back moth, lima-bean cutworm, tobacco cutworm and the like; dipteran injurious insects such as house fly, mosquito and the like; elytron injurious insects such as rice plant weevil, soy bean weevil, cucurbit leaf beetle and the like; roaches such as American cockroach, steam fly and the like; and mites such as two-spotted spider mite, kanzawa spider mite, citrus red mite and the like.

Especially, the insecticides according to the invention show a very excellent effect of controlling aphids such as cotton aphid, green peach aphid, foxglove aphid, cabbage aphid and the like; whiteflies such as greenhouse whitefly, sweet potato whitefly and the like; hemipteran injurious insects such as mulberry scale and the like; thrips such as southern yellow thrip and the like; and mites such as two-spotted spider mite, kanzawa spider mite, citrus red mite and the like.

The effect of the compounds according to the invention will be described with respect to the following test examples. Moreover, the following compounds were used as a comparative chemical. Comparative chemicals A to C are compounds disclosed in Research Disclosure RD 278004 and are used by the same formulation as described above, while comparative chemicals D and E are commercial products usually used for the control of aphids. Comparative chemical A: 3-(2-chlorophenyl)-5-(2-chloropyridin-3-yl)-1-methyl-1H-1,2,4-triazole Comparative chemical B: 3-(2-chlorophenyl)-5-(6-chloropyridin-3 -yl)-1-methyl-1H-1,2,4-triazole Comparative chemical C: 3-(2-chloro-4-fluorophenyl)-5-(6-chloropyridin-3 -yl)-1-methyl-1H-1,2,4-triazole Comparative chemical D: 45% wettable powder of Methomyl Comparative chemical E: 50% emulsion of Ethiophencarb

TEST EXAMPLE 1

Insecticidal test through immersion process

The wettable powder prepared according to Formulation Example 2 was diluted with water so that the concentration of the active ingredient was 0.8 ppm or 0.16 ppm. In the resulting diluted wettable powder were immersed cucumber seedlings previously inoculated with larvae of cotton aphid and then subjected to a drying treatment in air. After the treatment, the cucumber seedlings were placed in a thermostatic chamber of 25° C. for 3 days and then number of larvae died was counted to calculate the percentage of mortality. The test was carried out by double series. The results are shown in Table 2.

TABLE 2

| Compound No. | Mortality (%) | |
|---|---|---|
| | 0.8 ppm | 0.16 ppm |
| 1 | 100 | 65 |
| 3 | 100 | 60 |
| 6 | 100 | 100 |
| 7 | 100 | 100 |

TABLE 2-continued

| Compound No. | Mortality (%) | |
|---|---|---|
| | 0.8 ppm | 0.16 ppm |
| Comparative chemical A | 14 | 27 |
| Comparative chemical B | 100 | 35 |
| Comparative chemical C | 61 | 26 |

TEST EXAMPLE 2

Insecticidal test through injection process

The wettable powder prepared according to Formulation Example 2 was diluted with water so that the concentration of the active ingredient was 0.8 ppm or 0.16 ppm. The resulting diluted wettable powder was injected into a pot containing cucumber seedlings previously inoculated with larvae of cotton aphid. After the injection, the cucumber seedlings were placed in a thermostatic chamber of 25° C. for 3 days and then the number of larvae died was counted to calculate the percentage of mortality. The test was carried out by double series. The results are shown in Table 3.

TABLE 3

| Compound No. | Mortality (%) | |
|---|---|---|
| | 0.8 ppm | 0.16 ppm |
| 1 | 100 | 100 |
| 2 | 100 | 65 |
| 3 | 100 | 60 |
| 6 | 100 | 100 |
| 7 | 100 | 100 |
| Comparative chemical A | 85 | 0 |
| Comparative chemical B | 80 | 40 |
| Comparative chemical C | 65 | 35 |

TEST EXAMPLE 3

Test for systemic translocation control through soil improving treatment process Granules prepared according to Formulation Example 4 (0.5 kg per 10 are) were applied to stub roots of cucumber seedlings platted in a pot and previously inoculated with aphid larvae. After the treatment, the pot was placed in a green house, during which the number of living adults and larvae was counted every 7 days. The test was carried out by triple series. The results are shown in Table 4.

TABLE 4

| Compound No. | Number of living adults and larvae | | |
|---|---|---|---|
| | before treatment | days after treatment | |
| | | 7 days | 14 days |
| 7 | 40 | 5 | 0 |
| Comparative chemical A | 35 | 89 | 27 |
| Comparative chemical B | 40 | 321 | 433 |
| Comparative chemical D | 39 | 26 | 108 |

TABLE 4-continued

| Compound No. | Number of living adults and larvae | | |
|---|---|---|---|
| | before treatment | days after treatment | |
| | | 7 days | 14 days |
| non-treated | 32 | 427 | 392 |

TEST EXAMPLE 4

Test for systemic penetrance control through spraying process on stem and leaves The wettable powder prepared according to Formulation Example 2 was diluted with water so that the concentration of the active ingredient was 100 ppm. The resulting diluted wettable powder was sprayed onto only front sides of leaves in cucumber seedlings platted in a pot and previously inoculated at their back sides with aphid larvae without being sprayed onto the back sides. After the treatment, the pot was placed in a green house, during which the number of adults and larvae living in the back sides was counted every 5 days. The test was carried out by triple series. The results are shown in Table 5.

TABLE 5

| Compound No. | Number of living adults and larvae | | | |
|---|---|---|---|---|
| | before treatment | days after treatment | | |
| | | 5 days | 10 days | 15 days |
| 7 | 31 | 0 | 6 | 8 |
| Comparative chemical A | 32 | 50 | 327 | 283 |
| Comparative chemical B | 29 | 4 | 10 | 71 |
| Comparative chemical E | 32 | 95 | 420 | 289 |
| non-treated | 31 | 151 | 323 | 128 |

What is claimed is:

1. A triazole derivative having the following formula [I]:

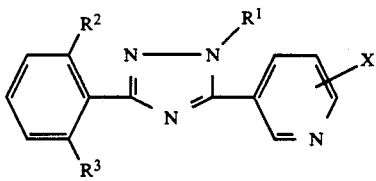

wherein $R^1$ is a lower alkyl group, $R^2$ and $R^3$ are same or different halogen atoms and X is a chlorine atom located at 2- or 6-position).

2. A triazole derivative according to claim 1, wherein said $R^1$ in the formula [I] is selected from methyl group, ethyl group, propyl group, isopropyl group, butyl group, isobutyl group, t-butyl group and s-butyl group, and each of said $R^2$ and $R^3$ in the formula [I] is selected from fluorine, chlorine, bromine and iodine.

3. A triazole derivative according to claim 1, wherein said $R^1$ in the formula [I] is a methyl group or an ethyl group.

4. An insecticide containing an insecticidally effective amount of a triazole derivative claimed in claim 1 as an active ingredient and a member selected from the group consisting of a carrier, a surfactant, a dispersing agent and an adjuvant.

* * * * *